United States Patent [19]
Timmons

[11] Patent Number: 5,597,966
[45] Date of Patent: Jan. 28, 1997

[54] FLUID SAMPLING DEVICE

[76] Inventor: Robert D. Timmons, R.F.D. Meadowdale Rd., Prairie Du Sac, Wis. 53578

[21] Appl. No.: 456,486

[22] Filed: Jun. 1, 1995

[51] Int. Cl.⁶ ................................................. G01N 1/12
[52] U.S. Cl. ........................... 73/864.63; 73/863.72
[58] Field of Search ..................... 73/864.63, 863.71, 73/864.65, 864.66, 864.67, 863.72

[56] References Cited

U.S. PATENT DOCUMENTS

| | | | |
|---|---|---|---|
| 4,050,315 | 9/1977 | Markfelt . | |
| 4,271,704 | 6/1981 | Peters | 73/864.63 |
| 4,367,657 | 1/1983 | Ward | 73/864.65 X |
| 4,590,810 | 5/1986 | Hunkin et al. | 73/864.63 |
| 4,625,574 | 12/1986 | Robbins | 73/864.63 |
| 4,888,999 | 12/1989 | Kozak | 73/864.65 |
| 4,928,541 | 5/1990 | Toon et al. | 73/864.63 |
| 4,949,582 | 8/1990 | Vollweiler | 73/864.63 |
| 5,139,654 | 8/1992 | Carpenter | 210/136 |
| 5,341,692 | 8/1994 | Sher et al. | 73/864.63 |
| 5,341,693 | 8/1994 | Banu | 73/864.63 X |
| 5,349,875 | 9/1994 | Sher et al. | 73/864.65 |
| 5,507,194 | 4/1996 | Scavuzzo et al. | 73/864.63 |

*Primary Examiner*—Thomas P. Noland
*Attorney, Agent, or Firm*—Shlesinger, Arkwright & Garvey

[57] ABSTRACT

An bailer apparatus for collecting a sample from a body of fluid comprising an elongated hollow body receptacle having first and second ends and defining a chamber therebetween. A valve device is provided for permitting fluid to enter the chamber and be retained therein as a collected sample. At least a portion of the bailer is constructed from an inert, high density plastic material having a specific gravity greater than water, the overall specific gravity of the apparatus being greater than the specific gravity of the body of fluid to be sampled so as to cause the apparatus to sufficiently sink for sample collection.

19 Claims, 1 Drawing Sheet

FLUID SAMPLING DEVICE

FIELD OF THE INVENTION

The present invention relates to an improved apparatus for obtaining a representative sample from a body of fluid and in particular, a sample of water from an environmental monitoring well.

BACKGROUND OF THE INVENTION

In recent years it has become increasingly common to monitor groundwater for evidence of pollution. This involves positioning a monitoring well in the suspected area and routinely extracting samples from such wells for laboratory analysis. It is critical the sample be extracted in a manner that will eliminate any possibility of contamination.

The sampling device is conventionally referred to as a "bailer" and comprises an elongated tube having at least one opening for entry of the water sample into a collection chamber. A valve or other mechanism is also provided to trap the water within the collection chamber after sampling.

Prior art bailers are rather complicated in design and must be carefully cleaned after use to prevent contamination of the samples. As a result, it has become common in the industry to employ disposable or "throw-away" bailers that are discarded after a single use.

Throw-away bailers are often manufactured from inexpensive and lightweight materials such as plastic. The use of plastics or other low density material in bailer construction has heretofore required the addition of a weight that enables the device to sink within the fluid being sampled. Typically, such weighing has involved the addition of metal to the bailer. For example, U.S. Pat. No. 4,050,315 to Markfelt discloses a chamber filled with lead shot positioned at one end of a bailer. It is also known to incorporate flanges within the inside wall of the bailer tube for securing a coated steel nut or metal washer.

As is apparent, a bailer that requires supplemental weights raises manufacturing expenses and renders the device difficult to recycle. More significantly, the incorporation of a reactive metal material within the bailer increases the likelihood of contamination to the sample. While these prior art devices are suitable for certain sampling applications, they are not acceptable when highly accurate sampling is required.

A need has therefore existed in the art for a throw-away bailer device constructed from an inert materials that does not require extrinsic weighing attachments.

OBJECTS AND SUMMARY OF THE INVENTION

It is therefore an object of the present invention to provide a disposable bailer device constructed entirely from inert plastic material without the need for attachment of supplemental weights.

A further object of the present invention is to provide a bailer device constructed entirely from an inert material such as polyethylene and therefore avoid contamination of the sample from the bailer.

A still further object of the present invention is to provide a bailer device that, due to the construction from plastic materials may be inexpensively manufactured, disposed of after a single use and readily recycled.

A further object of the present invention is to provide a bailer device constructed entirely from plastic material and whereby at least a portion of the device is constructed from a high density plastic material having a specific gravity greater than water to cause the device to sink without the need to attach complicated supplemental weight structures to the device.

A still further object of the present invention is to provide a bailer device whereby the weighted portion of the bailer may be the bailer tube wall or the end caps or any portion of the device without the need to modify the bailer design or change the manufacturing process in any way other than resin substitution.

A still further object of the present invention is the provide a bailer device that may be readily modified to vary sampling depth or to allow sampling in a fluid other than water through the selection of a resin having a different density.

In summary, the present invention is directed to an apparatus for collecting a sample from a body of fluid comprising an elongated hollow body receptacle having first and second ends defining a collection chamber therebetween, means for permitting fluid to enter the chamber and be retained therein as a collected sample and at least a portion of the hollow body receptacle comprising a high density plastic having a specific gravity greater than water, the hollow body receptacle having an overall specific gravity greater than the specific gravity of the body of fluids to be sampled so as to enable the apparatus to sink and collect fluid therein.

The manner in which these as well as other objects of the present invention can be accomplished will be apparent from the following detailed description and examples.

DETAILED DESCRIPTION OF THE PREFERRED EMBODIMENT

Figure 1:
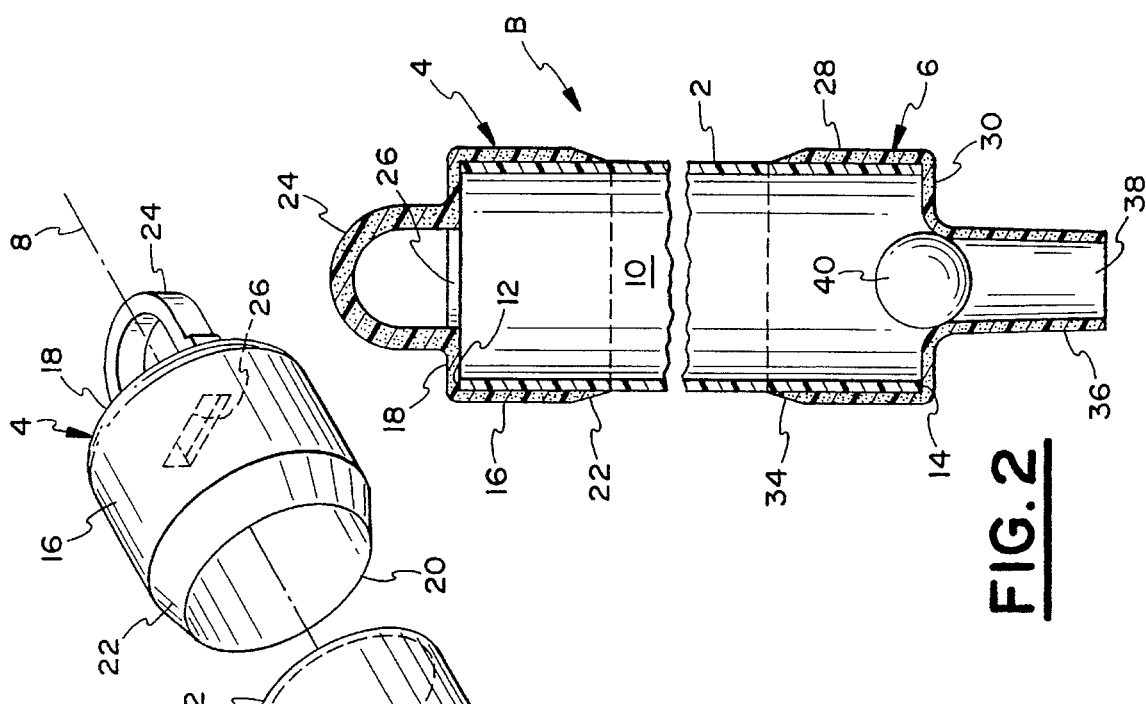
FIG. 1 is an exploded perspective view of a bailer device according to the present invention with the elongated hollow body receptacle shown having an indeterminant length.

Referring to FIG. 1, the bailer device B according to the present invention is shown including an elongated hollow body receptacle 2, an upper end cap 4 and a lower end cap 6 generally aligned along a central axis 8.

The elongated hollow body receptacle 6 is shown of indeterminant length but in the preferred embodiment has a length between about two feet to about seven feet depending upon the quantity of sample to be collected. The hollow body receptacle 2 is shown as a tubular wall defining a central chamber 10 therein and having a first end 12 and a second end 14. It is within the scope of the present invention to configure the hollow body receptacle 2 in a shape other than an elongated tube depending upon the sample required or other factors.

Figure 3:
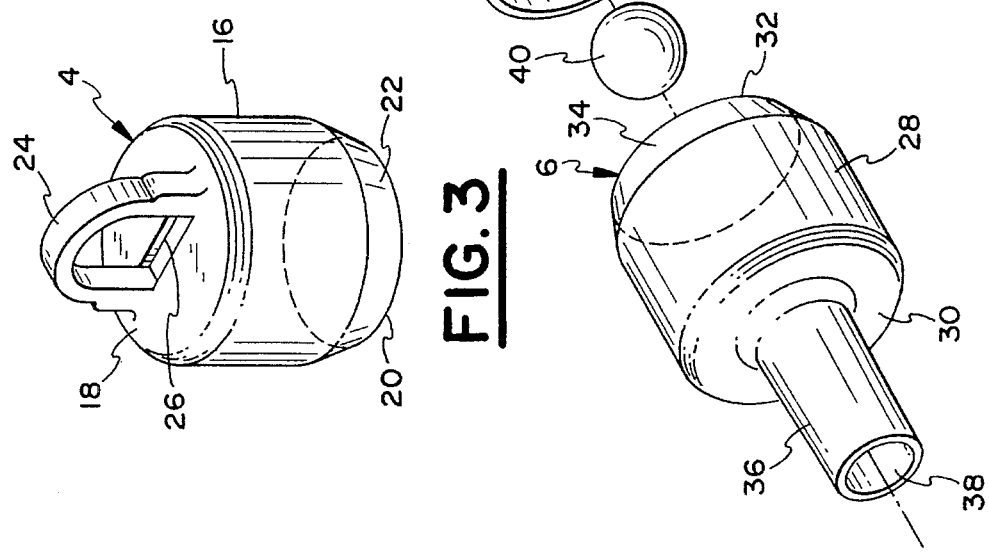
FIG. 3 is a perspective view illustrating the upper end cap according to the present invention.

As best shown in FIGS. 1 and 3, the upper end cap 4 comprises an annular side wall 16, a top surface 18 and an open end 20. The side wall 16 includes a chamfered bottom portion 22 terminating at the open end 20. As can be appreciated, open end 20 is configured to receive in a fluid-tight manner either of the first end 12 or second end 14 of elongated hollow body receptacle 2. A bail member 24 is disposed on the top surface 18 of upper end cap 4 to enable a hook or other securing means (not shown) to be attached to the device B for the purpose of lowering and raising the bailer B into a well or other body of liquid to be sampled. A sampling passage 26 extends through the upper end cap 4 allowing entry of liquid into the bailer device B.

Returning now to FIG. 1, the lower end cap 6 is shown and includes a side wall 28, a top surface 30 and an open end portion 32. A chamfered bottom portion 34 is also provided in the manner as set forth for the upper end cap 4 described above. A cylindrical fitting 36 extends from the top surface 30 of lower end cap 6 and provides an opening or passageway 38 extending into the interior of bailer device B.

A ball valve 40 is provided and retained within the bailer device B to retain the collected sample within the device once a sufficient sample has been obtained. The ball valve 40 ordinarily has a diameter slightly greater than the diameter of passageway 38 to enable the passageway 38 to be sealed once the valve 40 moves into the closed position. As is apparent, other valve devices may be employed and each are intended to be within the scope of the present invention.

In a preferred embodiment of the present invention, the end caps 4 and 6 as well as the hollow body receptacle 2 are constructed from an inert material such as plastic. An "inert" material within the meaning of the present invention is a material that is resistant to chemical or physical action. In other words, the construction materials of the present bailer device will not interact with or affect the integrity of the collected sample. For example, if the bailer according to the present invention is employed to collect a liquid containing corrosive compounds, the inert construction of the central chamber 10, the end cap 4 and the end cap 6 will prevent any chemical or physical reaction with the collected sample. A representative inert plastic material according to the present invention is polyethylene, a thermoplastic resin capable of extrusion or molding into the various bailer components.

At least a portion of the inert plastic material in accordance with the present invention is a high density plastic e.g. high density polyethylene, having a density sufficiently greater than the density of the fluid being sampled to cause the entire bailer device to sink within the fluid being sampled. Ordinarily this fluid is water, however other fluids may be sampled by the device according to the present invention and the high density plastic may be modified accordingly to enable the bailer to sufficiently sink therein.

In the preferred embodiment, this high density polyethylene or other plastic material will have a specific gravity greater than about 1.20 g/cm$^3$. Applicant has determined that selection of this high density polyethylene or other plastic material having a similar density for the construction of the end caps 4 and 6 will provide the requisite density to enable the overall device to sink below the surface of the water that is to be sampled. By way of comparison, conventional polyethylene has a specific gravity less then about 0.90 g/cm$^3$ and would therefore not function as a "high density" plastic within the meaning of the present invention. However, such conventional polyethylene or other plastic material having a density less than the fluid to be sampled is suitable for construction of the remaining portion of the bailer. For example, if the end caps 4 and 6 are formed of the high density plastic material within the meaning of the present invention, the balance of the device i.e. the hollow body receptacle 2, may be constructed from any conventional (lower density) polyethylene. In yet another embodiment of the present invention, the entire bailer device is constructed from high density plastic material having a specific gravity greater than the fluid to be sampled.

Preferred polyethylene or other plastic materials having a density within the range of the present invention are the so called "filled" plastics. Filled plastics such as polyethylene incorporate powdered non-metallic material into the resin to increase density without compromising the physical properties of the resin. Non-metallic filler compounds within the scope of the present invention include but are in no way limited to powdered calcium carbonate, alumina hydrate, aluminum sodium carbonate, calcium phosphate, kaolinite clay, mica, talc, graphite, glass and silica. Filled plastic resins suitable for injection molding and forming are readily available from a variety of commercial manufacturers of thermoplastic resins and the like.

A preferred high density plastic material according to the present invention is manufactured and marketed by Dupont Canada Inc., Modified Polymers Business Unit, Ontario, Canada under the tradename ZEMID 600 series reinforced resins. This polyethylene resin is readily available at a density of about 1.20 g/cm$^3$, a significantly greater density than conventional so called "high density" polyethylene resins. ZEMID 600 and other linkage-modified polyethylenes are able to provide exceptionally greater densities than conventional high density polyethylenes by first oxidizing the base monomer to give it a polarity prior to polymerization. The oxidation causes the monomers to be more reactive with the filler during polymerization resulting in an end product resin having high specific gravity and enhanced toughness and stiffness.

Other high density resins are within the scope of the present invention. For example, any filled polyolefin compound may be selected so long as the end polymer has a specific gravity greater then water or the fluid to be sampled. In this way, the bailer device B according to the present invention will be caused to sink a predetermined depth without the need for various extraneous weighing systems such as metal nuts, shot or other prior art material. Any process whereby a polyolefin is polymerized directly with the finely-divided inert filler particles or where the filler is added after polymerization are included within the scope of the present invention. As can be appreciated, the quantity of filler will vary depending upon the desired specific gravity of the end product. Also, the filler must be rendered as inert as the plastic in which it is incorporated.

The plastic material within the scope of the present invention may be fabricated into the various parts of the bailer device B by injection molding or other forming means known in the art. As noted above, in the preferred embodiment the upper end cap 4 and the lower end cap 6 are constructed the high density polyethylene having a specific gravity greater then 1.20 g/cm$^3$ and the remaining portions of the bailer device i.e. the elongated hollow body receptacle 2, may be constructed from conventional polyethylene.

Figure 2:
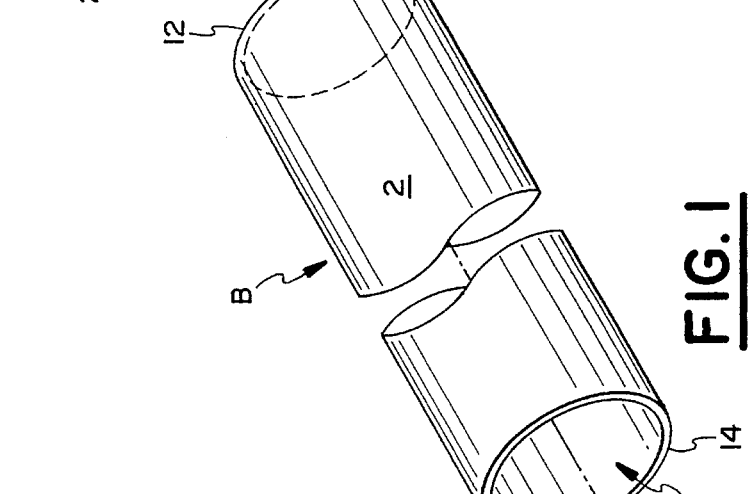
FIG. 2 is a cross-sectional view of the assembled bailer device according to the present invention illustrating the ball valve in the closed position and with the elongated hollow body receptacle having an indeterminant length.

As best shown in FIG. 2, once the bailer device B is assembled, the high density upper end cap 4 and the lower end cap 6 are spot welded or otherwise secured to the respective ends 12 and 14 of the hollow body receptacle 2. The ball valve 40 is contained within the chamber 10.

During operation, the bail member 24 is attached to a line (not shown) and the empty bailer device B is lowered into the body of fluid to be analyzed. Once the bailer device reaches the body of fluid to be sampled, it will sink because portions of the bailer device B have a specific gravity greater then the fluid to be sampled. During the descent, the ball valve 40 opens allowing liquid to pass into the central chamber 10 through passageways 38 and 26 displacing air which escapes from the bailer device B. After the predetermined depth has been reached, the bailer is lifted causing the ball valve 40 to close passageway 38 as illustrated in FIG. 2. As a result, the bailer device B may be retrieved immediately, the valve remaining closed during upward return of the bailer device and providing a sample of the fluid taken at the pre-determined depth.

After use, the bailer may be disposed of thereby eliminating the need for cleaning and possible contamination of subsequent samples.

The device according to the present invention may be constructed in a variety of sizes and shapes. Most commonly, the bailer will have a length of about two feet to about seven feet and a diameter of about three quarters of an inch to about four inches. In other applications, different sizes may be required and the present device is not limited to any specific dimension.

The device of the present invention has been found to be extremely effective over a wide range of depths and yields a highly accurate water sample that will not be compromised by the bailer construction materials. Further, spacers, shot or additional weights are not required thereby making the bailer according to the present invention economical to construct with less likelihood of failure during use.

As can be appreciated, it is within the scope of the present invention to make portions of the bailer B other than the end caps 4 and 6 of high density polyethylene. What is necessary is that the portions of the bailer constructed from high density, polyethylene or other plastic material be sufficient to cause the entire bailer device B to sink below the surface of the fluid to be sampled at the required depth.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

What is claimed is:

1. An apparatus for collecting a sample from a body of fluid comprising:
   a) an elongated hollow body receptacle having first and second ends and defining a chamber therebetween;
   b) means for permitting fluid to enter said chamber and be retained therein as a collected sample; and
   c) at least a portion of said hollow body receptacle comprising a high density plastic, said high density plastic is a polyolefin having a specific gravity greater than about 1.20 g/cm$^3$ whereby said hollow body receptacle having an overall specific gravity greater than the specific gravity of the body fluid to be sampled enabling said receptacle to sink and fluid to be collected therein.

2. An apparatus as in claim 1 and wherein:
   a) said first and second ends including first and second end cap portions respectively.

3. An apparatus as in claim 2 and wherein:
   a) said fluid permitting means comprising at least one fluid passageway extending into said chamber and a valve device for closing said at least one fluid passageway.

4. An apparatus as in claim 3 and wherein:
   a) said valve device is a ball check valve.

5. An apparatus as in claim 1 and wherein:
   a) said high density plastic is a filled polyeolefin.

6. An apparatus as in claim 5 and wherein:
   a) said polyolefin is filled with a powdered material selected from the group consisting of calcium carbonate, alumina hydrate, aluminum sodium carbonate, hydroxyapatite, calcium phosphate, kaolinite clay, mica, talc, graphite, glass, and silica.

7. An apparatus as in claim 1 and wherein:
   a) said high density plastic is a reinforced polyolefin.

8. An apparatus as in claim 1 and wherein:
   a) said at least a portion of said hollow body receptacle is at least one of said first and second ends.

9. A fluid sampling device as in claim 1 and wherein:
   a) said polyolefin is selected from the group consisting of polyethylene, polypropylene, polycarbonate, ABS and nylon.

10. A fluid sampling device as in claim 1 and wherein:
    a) said entire apparatus is chemically inert.

11. An apparatus for collecting a sample from a body of fluid comprising:
    a) an elongated hollow body having first and second ends forming a chamber therebetween, said elongated body is formed from a polyethylene material;
    b) a valve device for permitting fluid to enter said hollow body and be retained therein as a collected sample; and
    c) at least a portion of said elongated body is formed from a polyethylene material having a specific gravity greater than about 1.20 g/cm$^3$ whereby when said apparatus is placed in a body of water it will be caused to sink thereby enabling a water sample to be collected therein.

12. An apparatus as in claim 11 and wherein:
    a) said first and second ends including first and second end cap portions respectively.

13. An apparatus as in claim 12 and wherein:
    a) said valve device including at least one fluid passageway extending into said chamber and a ball for closing said at least one fluid passageway.

14. An apparatus as in claim 13 and wherein:
    a) said valve device is a check valve.

15. An apparatus for collecting a sample from a body of fluid comprising:
    a) an elongated hollow body having first and second end caps forming a chamber therebetween;
    b) valve device for permitting fluid to enter said chamber and be retained therein as a collected sample; and
    c) at least one of said first and second end caps is formed from a filled polyolefin material having a specific gravity greater than water, said apparatus having an overall specific gravity greater than the specific gravity of the body of fluid to be sampled whereby when said apparatus is placed in a body of fluid it is caused to sink.

16. An apparatus as in claim 15 and wherein:
    a) said filled polyolefin has a specific gravity greater than about 1.20 g/cm$^3$.

17. An apparatus as in claim 15 and wherein:
    a) said filled polyolefin is filled with a powdered material selected from the group consisting of calcium carbonate, alumina hydrate, aluminum sodium carbonate, hydroxyapatite, calcium phosphate, kaolinite clay, mica, talc, graphite, glass, and silica.

18. An apparatus as in claim 15 and wherein:
a) said filled polyolefin is selected from the group consisting of polyethylene, polypropylene, polycarbonate, ABS and nylon.

19. An apparatus as in claim 15 and wherein:
a) said valve device comprising at least one fluid passageway extending into said chamber and a ball adapted to selectively close said at least one fluid passageway.

* * * * *